(12) United States Patent
Morita et al.

(10) Patent No.: US 7,884,265 B2
(45) Date of Patent: Feb. 8, 2011

(54) HIGH REBAUDIOSIDE-A PLANT

(76) Inventors: Toyoshige Morita, 23-22 Teratani-Cho, Takatuki (JP); Koji Morita, 4-11-45 Tsurumi, Tsurumi-Ku Osaka (JP); Koichiro Komai, 38 Omiyayakushiyamahigashi-Machi Kita-Ku, Kyoto (JP)

( * ) Notice: Subject to any disclaimer, the term of this patent is extended or adjusted under 35 U.S.C. 154(b) by 605 days.

(21) Appl. No.: 11/815,400

(22) PCT Filed: Mar. 2, 2006

(86) PCT No.: PCT/JP2006/303992
§ 371 (c)(1),
(2), (4) Date: Aug. 2, 2007

(87) PCT Pub. No.: WO2006/093229
PCT Pub. Date: Sep. 8, 2006

(65) Prior Publication Data
US 2009/0214753 A1 Aug. 27, 2009

(30) Foreign Application Priority Data
Mar. 4, 2005 (JP) .............................. 2005-060930

(51) Int. Cl.
*A01H 1/00* (2006.01)
*A23L 1/236* (2006.01)
(52) U.S. Cl. .................. 800/298; 800/260; 426/548
(58) Field of Classification Search ................... None
See application file for complete search history.

(56) References Cited

U.S. PATENT DOCUMENTS

| | | | |
|---|---|---|---|
| PP10,564 P | 8/1998 | Marsolais et al. | |
| 6,031,157 A | 2/2000 | Morita et al. | |
| 6,080,561 A | 6/2000 | Morita et al. | |
| 6,255,557 B1 * | 7/2001 | Brandle | ...................... 800/298 |

FOREIGN PATENT DOCUMENTS

| | | |
|---|---|---|
| CN | 1212827 | 4/1999 |
| CN | 1327720 | 12/2001 |
| CN | 1547893 | 11/2004 |
| CN | 101213935 | 7/2008 |
| JP | 59045848 | 3/1985 |
| JP | 60160823 | 8/1985 |
| JP | 61202667 | 9/1986 |
| JP | 6296025 | 5/1987 |
| JP | 10271928 | 10/1998 |
| JP | 200032859 | 2/2000 |
| JP | 2002262822 | 9/2002 |
| JP | 2003-9878 A * | 1/2003 |
| JP | 20039878 | 1/2003 |
| WO | WO 99/49724 | 10/1999 |

OTHER PUBLICATIONS

English Translation of JP-2003-9878-A (Feb. 2010).*
Search Report for WO2006093229, May 23, 2006, Morita Kagaku Kogyo.
Suzuki, F.R., and Dobberstein, R.H., Plant Variety Protection Certificate No. 8200065, *Stevia rebaudiana* Bertoni, Variety P.J. Suzuki, Issued Oct. 28, 1982.
Hata, S., et al., Breeding of triploid plants of stevia (*Stevia rebaudiana* Bertoni) with high rebaudioside A content. Japanese Journal of Tropical Agriculture 45:281-289 (2001).
Han, Y., et al., Selection of elite individual plants of *Stevia rebaudiana* Bertoni. Journal of Plant Sciences and Environment 11:25-28 (2002).
Search Report for EP 06715101, Nov. 10, 2005, Morita Kagaku Kogyo Co., Ltd.

* cited by examiner

*Primary Examiner*—David H Kruse
(74) *Attorney, Agent, or Firm*—Baker & McKenzie, LLP

(57) ABSTRACT

A novel plant belonging to the *Stevia Rebaudiana Bertoni* variety which contains at least 4 parts by weight or more of Rebaudioside A with respect to one part by weight of Stevioside, and allows a sweetener of a good quality to be easily produced from said plant or dried leaves thereof.

11 Claims, 1 Drawing Sheet

HIGH REBAUDIOSIDE-A PLANT

PRIOR RELATED APPLICATIONS

This application claims priority to WO2006093229, filed Feb. 2, 2006 and JP2005-060930 Filed Apr. 3, 2005. Each is incorporated by reference in its entirety.

FEDERALLY SPONSORED RESEARCH STATEMENT

Not applicable.

REFERENCE TO MICROFICHE APPENDIX

Not applicable.

FIELD OF THE INVENTION

The present invention relates to a plant belonging to the variety of *Stevia Rebaudiana Bertoni* with a high content ratio of Rebaudioside-A compared with Stevioside, and a method for the production of a sweetener extracted from said plant and/or its dried leaves. In addition, the present invention is related to a method to produce Rebaudioside A of high purity from said sweetener.

BACKGROUND OF THE INVENTION

*Stevia* is a perennial plant of the Compositae Asteraceae originally grown in Paraguay, South America, and its scientific name is *Stevia Rebaudiana Bertoni*. *Stevia* contains sweet components having the sweetness of 300 times or more than that of sugar, and is planted for use as a natural sweetener obtained by the extraction of this sweetening components.

As the sweetening components, Stevioside ($C_{38}H_{60}O_{18}$), Rebaudioside A ($C_{44}H_{70}O_{23}$), Rebaudioside C, D and E, Dulcoside A etc. have been known. With the variety generally planted, Stevioside (ST) is the major component among the above-mentioned sweet components with a content amount of Rebaudioside A (RA) being about 3/10 to 4/10 that of Stevioside and that of Rebaudioside C being slightly less, but depending on varieties, there is *Stevia* with Rebaudioside C being the major component. That is, there are various varieties.

Among the tastes such as bitterness and astringency, sweetness is very delicate. Since Stevioside has a degree of sweetness of 300 times that of sugar, it has been used as a natural sweetener in the food industry. Its sweetness is relatively similar to that of sugar, however, there is a defect in that an unpleasant taste such as bitterness remains in the mouth. Therefore, it is not desirable for a sweetener to contain a large amount of Stevioside. On the other hand, Rebaudioside A has sweetness of a good quality and a degree of sweetness of 1.3 to 1.5 time that of Stevioside.

It is thus necessary to reduce the production cost of Rebaudioside A, to maintain the stable yield of dried leaves, to develop a variety of *Stevia* which contains a high content amount of Rebaudioside A having excellent sweetening quality as a sweetening raw material, and at the same time, to maintain its continuous supply and to produce an excellent sweetener based on these.

The inventors of the present invention carried out plant breeding through the repetition of selective cross fertilizations of conventional varieties, thereby obtaining *Stevia* varieties with a high content ratio of Rebaudioside (RA) to Stevioside (ST), and sweeteners excellent in content ratio of Rebaudioside A to Stevioside (ST) have been produced by extracting sweetening component from these plants (see Patent Literatures 1-1 through 1-3 to be described later), however, development of varieties stably with a higher and better content ratio of Rebaudioside A has been desired.

On the other hand, in plant breeding of *Stevia* plants, an issue is a method of identification of *Stevia* plants. As an identification method of improved *Stevia* plants, we may think of identifications by plant heights, shapes of leaves, etc., however, as *Stevia* is self non-compatible and tends to become hybrids, classification only by plant heights, shapes of leaves, etc. can not achieve this.

In addition, there exist comparative identification based on the disease resistance to pathogens specific to *Stevia*, however, although dead leaves and black leaf spots which occur specifically to *Stevia* are caused by *Septoria* fungus and *Alternaria*, these fungi live in soil. Therefore, since these symptoms occur not only in Japan but also throughout the world, these characteristics alone are insufficient for the identification of a variety.

With an improved variety with a high sweetening content and a high content ratio of Rebaudioside A in comparison with Stevioside, one may think of identification method by this content ratio, however as a variation in sweetening content ratio may inevitably vary depending on a weather condition during the growth period, a harvesting time, etc., this method lacks practicality.

Recently, a method by which to make identification through DNA identification based on the RAPD method which uses a primer mix (see Patent Reference 2 below) has been developed, however, it is not clear whether or not it is possible to apply this to the identification of a plant in accordance with the present invention.

Patent Reference 1: Laid Open Patent Publication Sho. 59/1984-045848 Gazette
Patent Reference 2: Laid Open Patent Publication Sho. 60/1985-160823 Gazette
Patent Reference 3: Laid Open Patent Publication Sho. 61/1986-202667 Gazette
Patent Reference 4: Laid Open Patent Publication No. 2003-9878 Gazette

SUMMARY OF THE INVENTION

Abbreviations: ST=Stevioside; RA=Rebaudioside A

The present invention is to create varieties excellent in sweetening component content amount and sweetening component content ratio, to enable to distinguish genes thereof by the RAPD method to maintain the characteristics thereof, thereby differentiating them from *Stevia* plants of other varieties, and to provide sweeteners excellent in sweetening property and a method for the production thereof.

The first aspect of the present invention relates to a *Stevia Rebaudiana Bertoni* variety which contains 4 parts by weight or more of Rebaudioside A with respect to one part by weight of Stevioside. For this, as will be described later, by repeating crossbreeding and selection, new plants belonging to *Stevia Rebaudiana Bertoni* variety was created which contains at least 4 parts by weight of Rebaudioside A with respect to one part by weight of Stevioside.

The second aspect of the present invention relates to a method for the production of a sweetener which contains 4 parts by weight or more of Rebaudioside A with respect to one part by weight of Stevioside, said method for the production being characterized by performing extraction from the plant described in the previous paragraph or dried leaves thereof with water or a water-containing solvent.

The third aspect of the present invention relates to a method for the production of a high purity sweetener which contains 40 parts by weight or more of Rebaudioside A with respect to one part by weight of Stevioside; said method for the production of a sweetener which contains 40 parts by weight or more of Rebaudioside A with respect to one part by weight of Stevioside, the content thereof being 92% or higher, being characterized by performing re-crystallization of the sweetener obtained in the previous paragraph.

In an improvement of a variety through crossbreeding and selection, the identification method of a variety selected has an important meaning. The inventors of the present invention have studied identification methods based on DNA identification by the RAPD method.

The present invention provides a sweetener excellent in sweetening quality and a method for the production thereof.

BRIEF DESCRIPTION OF THE DRAWINGS

a: I lind III marker
b and e: SN variety
c and f: Morita variety
d and g: SS variety
h: 1 kbp DNA ladder marker

Figure 1:
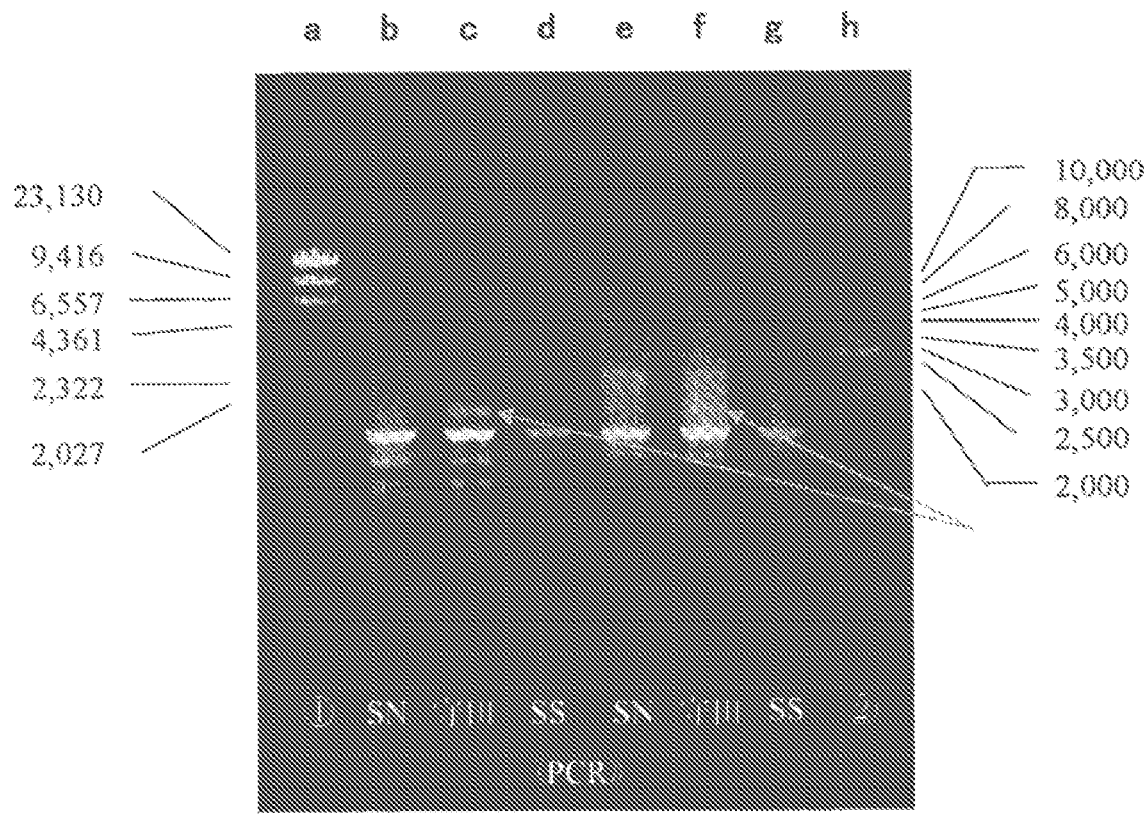
FIG. 1 is an electrophoresis diagram of the DNA base sequences of the Morita variety, SS and SN. The characteristic base sequences are indicated with arrows. The symbols in FIG. 1 are as follows.
Figure 2:
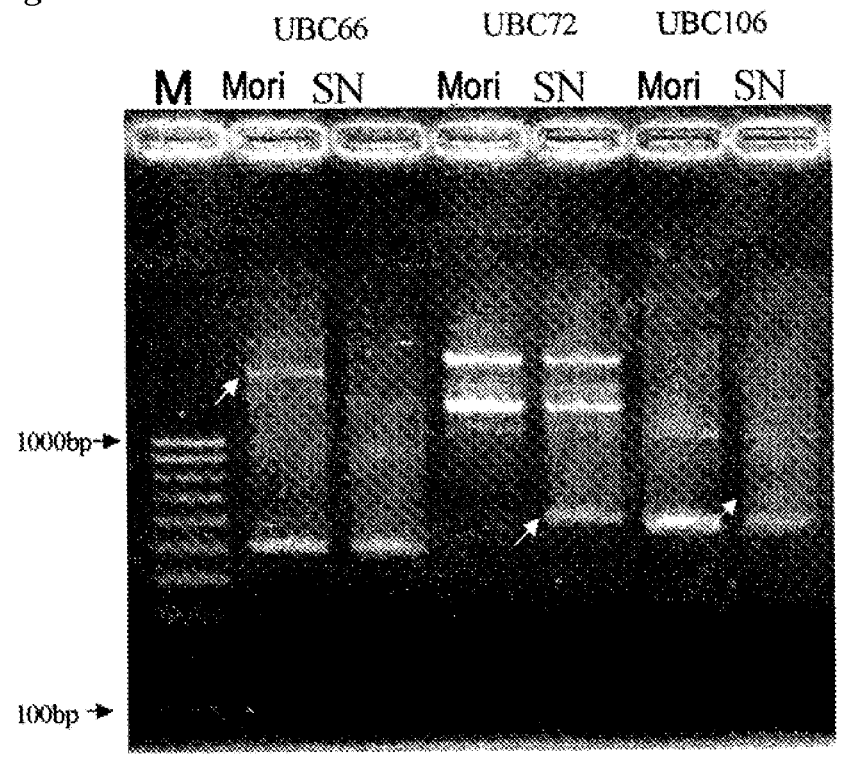
FIG. 2 is an electrophoresis diagram of the DNA base nucleotide sequence of the Morita variety and SN. The characteristic base sequences are indicated with arrows. The symbols in FIG. 2 are as follows.

Mori: Morita variety
SN: SN variety
M: DNA marker (100 bp ladder)

DESCRIPTION OF EMBODIMENTS OF THE INVENTION

The RAPD method (random amplified polymorphic DNA method) used for the identification in the present invention is one of the analytical methods of DNA, and it is a method for the analysis by electrophoresis of a DNA pattern amplified in a DNA region sandwiched between the same or similar sequences as or to the primers used in a PCR reaction (Polymerase chain reaction) using a plural number of primers. In addition, for cetyl trimethyl ammonium bromide (CTAB) is a quaternary ammonium salt having a long chain alkyl group, and it forms an insoluble complex with a poly anion such as nucleic acid, it can be utilized for isolating a nucleic acid.

In the means by which to classify a variety based on differences in DNA, a genome DNA is singly isolated from a plant by CTAB, ribonucleic acid (RNA) is removed, and a PCR amplified product obtained by the PCR method by use of a primer mix is distinguished by the differences in DNA finger print obtained by the agarose gel electrophoresis method. In the case of the plant in accordance with the present invention, as will be described later, it has been confirmed that a characteristic base sequence is shown at the 2000 bp lower portion.

In reality, with the genome DNA selectively precipitated as a pattern with respect to the raw material plant, a 35 cycle reaction is carried out at 94 degrees (30 sec), 55 degrees (30 sec), and 72 degrees (120 sec) by use of a set of, for example, A06 (base sequence: ACTGGCCGAGGG) and A48 (base sequence: CCGCAGGGACCA) as primers and rTaq (Takara), and thereafter, a reaction is allowed to take place for 10 min at 72 degrees. After this, the PCR amplified product is confirmed by the agarose gel electrophoresis method, and thus the plant can be confirmed by a specific DNA band For the production of a sweetener, next, said plant or dried leaves thereof are subjected to extraction with water or a solvent containing water, the extract solution is concentrated as is or if necessary, ionic impurities are removed with an anionic exchange resin or a cationic exchange resin, or activated carbon, the sweetening components are allowed to be adsorbed into an adsorption resin, followed by the elution with a hydrophilic solvent, and the elute is concentrated, and dried to produce a sweetener. The method for the production of a sweetener can include customary refining means such as a discoloring step in addition to the above, as appropriately required, and a method by which to obtain high purity Rebaudioside A may include customary steps such as a membrane separation, extraction with alcohol, and crystallization etc. In addition, in the crystallization method, it is possible to appropriately use it by adding water to an organic solvent such as ethanol and methanol as a crystallization solvent. It is possible to add other natural or artificial sweeteners, a diluting agent, etc. to this sweetener thus obtained.

For the breeding, varieties which contain a relatively high concentration of Rebaudioside A are crossbred, and selected. First, SF5-1 and SF5-2 (described in, Laid Open Patent Publication No. Hei 10 1998-271928 No. 271928-1998 Gazette) which contain Rebaudioside A at a high concentration are artificially cross-bred, TD-1 (described in Laid Open Patent Publication No. 2003-9878 Gazette) is selected from the seeds thus obtain, which are further cross-bred artificially, a variety which has resistance to *Septoria* fungus and *Alternaria* fungus is selected from these seeds, the sweetening component thereof is analyzed, and a plant which contains 4 parts by weight or more of Rebaudioside A with respect to one part by weight of Stevioside, is high in sweetening content, and is relatively excellent in disease resistance is selected. Furthermore, the content amount of the sweetening components, the ratio of the sweetening components, and growth conditions are repeatedly observed, and this is named Morita variety whose genes were searched.

Furthermore, this time, the Applicant has completed the international deposit of the Morita variety concerning this invention (International Patent Organism Depositary (IPOD) No. FERM BP-10353). Therefore, it is possible to easily obtain the plant of said invention from the seeds of the Morita variety of the depository. *Stevia* is self incompatible, and although it is not necessarily true that the target plant can be always obtained from said seeds, the target plant can be easily selected by the DNA identification described in this Application. And if necessary, if it is cross-bred with other high quality *Stevia* variety (for example, TD-1) and selection is made in accordance with Embodied Example 1 to be described later, a plant which contains Rebaudioside A at a high concentration can be easily obtained. These plants are all covered in the plants which can be obtained from the seeds of the Morita variety internationally deposited, that is, the Morita variety.

In the following, the breeding process, the characteristics thereof, etc. will be specifically described. However, the present invention is not limited to these breeding processes and cultivating methods.

Example 1

Breeding and Tests

From the seeds obtained by cross breeding of varieties containing Rebaudioside A at a relatively high concentration, the seeds obtained by artificial cross breeding of SF-1 and SF 5-2 (described in Laid Open Patent Publication No. Hei 10/1998-271928) containing Rebaudioside A in a vinyl house in Nimi plant were sowed, the seedlings germinated were re-planted in seedling growing pots, and 600 seedlings of a height of about 8 cm or higher were transplanted in an agriculture land in the plant in early May, while about 20 kg each per are of fertilizer components of nitrogen, phosphorus and potassium were applied to the land. In early July, as additional fertilizers, 10 kg each of the fertilizer components of nitrogen, phosphorus and potassium per are were additionally applied to the land.

In early September, the sweetening components were analyzed, and stock, TD-1 variety (described in Laid Open Patent Publication No. 2003-9878) was selected that contains 3 times of more of Rebaudioside A with respect to Sterioside.

In 1998, the TD-1 variety was artificially cross bred in the vinyl house in Nimi plant, the seeds obtained were sowed in a vinyl house in Nimi plant in March of 1999, the seedlings germinated were re-planted in seedling growing pots, and 300 seedlings of a height of about 7 cm or higher were transplanted in an agriculture land in the plant in early May, while about 20 kg each per are of fertilizer components of nitrogen, phosphorus and potassium were applied to the land. In early July, as additional fertilizer, 10 kg each of the fertilizer components of nitrogen, phosphorus and potassium were additionally applied to the land.

In early September, the sweetening components were analyzed, and stock which contain 4 parts by weight or more of Rebaudioside A with respect to Stevioside, and is more superior in disease resistance and grow better than, TD-1 variety and were selected. In the middle of April of 2000, the 100 sprouts germinated from them were cut and planted. In early May, they were similarly planted in the agriculture land of the plant, and at the end of July, the disease resistance and growth thereof were investigated again, and that the sweetening component ratios and content amounts were superior was confirmed. Furthermore, for 3 years from 2001, it had been confirmed that the disease resistance, sweetening component ratios, sweetening component contents amount and the yield of dried leaves were superior and there was no change in growth and components, and this was named Morita variety.

In order to compare the Morita variety and other varieties, cuttings were made of 40 each of TD-1 (TD) whose main component was Rebaudioside A, and other general *Stevia* variety (SN) whose main sweetening component was Stevioside and whose secondary sweetening component was Rebaudioside A and they were planted similarly in the agriculture land in the plant.

The presence or absence of outbreak of any disease was investigated in each 10 varieties arbitrarily selected in early June out of the 200 seedlings of the Morita variety multiplied from the above-mentioned cuttings transplanted in the agriculture land in early May, and 40 seedlings each of the TD variety and the SN, and thereafter, the seedlings of the Morita, TD and SN seedling each were cut at the height of 15 cm above the ground, the leaves were separated and after drying, they were used as samples for analysis.

The results of the analysis are as follows.

TABLE 1

Comparison test 1 of the Morita variety, TD and SN

| Variety | Appearance of yellowed or blackened leaves | ST (%) | RA (%) | RA/ST |
|---|---|---|---|---|
| Morita | black spots in 0 stock | 2.3 | 9.3 | 4.04 |
| TD | black spots in 1 stock | 2.5 | 9.1 | 3.64 |
| SN | occurred in 7 stocks | 6.9 | 2.8 | 2.46 |

In the middle of July, additional fertilizers were applied, and after selecting 20 stocks from each variety per one section and investigating the onset conditions of the diseases due to *Septoria* fungus and *Alternaria*, each variety was cut from the sections above the ground, the leaves were separated and after drying, they were used as analytical samples.

The results of the analysis are as follows.

TABLE 2

Comparison test 2 of the Morita variety, TD and SN

| Variety | Appearance of yellowed or blackened leaves | ST (%) | RA (%) | RA/ST | Yield/plant (g) |
|---|---|---|---|---|---|
| Morita | black spots on the lower leaves in 3 stocks | 1.1 | 13.1 | 11.9 | 12.9 |
| TD | black spots on the lower leaves in 5 stocks | 1.1 | 11.1 | 10.0 | 11.7 |
| SN | withered of the lower leaves in 12 stocks | 9.8 | 3.9 | 0.39 | 9.3 |

With the Morita variety, the ratio of the occurrence of black spots on the lower leaves was relatively low, and it was superior to other varieties in sweetening component content, and dry leaves yield. With the TD variety, in comparison with the Morita variety, a large number of black spots of the lower leaves due to *Septoria* fungus were observed, the leaves began to be already yellowed due to *Septoria* fungus. The SN variety showed yellowing of the leaves up to the 3rd node of the lower leaves due to *Septoria* fungus, and the leaves at the first node withered.

In March of 2004, 200 cuttings of the tips of the ears sprouted from the Morita variety were planted, in the end of April, they were re-planted in the agriculture land, the sections above the ground were harvested at the end of May, the end of June, the end of July, the end of August, the end of September and the end of October after flowering, only the leaves were separated, and dried, and the sweetening component content amount was measured.

The sweet components were measured by the high performance liquid chromatography.

TABLE 3

Seasonal Stevioside and Rebaudioside-A Production

| Harvesting time | ST (%) | RA (%) | RA/ST |
|---|---|---|---|
| end of May | 2.2 | 9.1 | 4.1 |
| end of June | 2.3 | 9.6 | 4.2 |
| end of July | 1.9 | 12.6 | 6.6 |
| end of August | 1.5 | 12.8 | 8.5 |
| end of September | 1.0 | 13.2 | 13.2 |
| end of October | 1.0 | 10.1 | 10.1 |

The Morita variety showed different sweetening component content amount and sweetening component ratios depending on the growth period; a tendency was observed in which as the growth period becomes longer, the sweetening component content amount increased, and on the other hand, the Stevioside content amount decreased. At the end of October, which is the flowering time, the sweetening component content amount decreased.

In terms of the sweetening component content amount, sweetening component ratio and yield, as the Morita variety was the best, the Morita variety was identified by the PCR method.

A mortar sterilized by drying and heating was charged with about 0.2 g of the leaves of the Morita variety, to which liquid nitrogen was added, they were crushed by a pestle, and about 0.05 g at a time was put into micro tube(s) by a spatula. 300 µl of 2% CTAB solution (2% CTAB solution (50 ml): composition 100 mM, tris-HCl (pH 8.0) 20 mM, EDTA (pH 8.0), 2% CTAB, 1.4 M NaCl) was added thereto, and after tumbling and mixing, the tube was moved to a heat block heated to 65° C., and it was heated for 30 min. An equal amount (300 µl) of chloroform/isoamyl alcohol (24:1) was added thereto, followed by stirring gradually. After centrifuging and separating it at 14000 rpm for 15 min, the aqueous layer, which was the upper layer of the content separated into 2 layers, was moved to a new tube.

The operations after above-mentioned chloroform/isoamyl alcohol were repeated one more time, and an aqueous layer was moved to a new tube. 400 µl of 1% CTAB solution (1% CTAB solution (50 ml): composition 1 M, tris-HCl 2.5 mM, EDTA 1.0 ml, 1% CTAB 0.5 g) was added thereto, and after tumbling and mixing for 15 min, it was left to stand still at room temperature for 1 hr, followed by centrifugal separation at 14000 rpm for 15 min.

The supernatant was discarded, followed by the addition of 400 µl of 1 $MC_sCl$, and the precipitate was completely dissolved by pipetting. 900 µl of 100% ethanol was added thereto, and after tumbling and mixing, it was left to stand still at a temperature of –20° C. for 20 min, followed by centrifugal separation at 14000 rpm for 15 min. The supernatant was discarded, followed by the addition of 400 µl of 70% ethanol to the precipitate, it was subjected to centrifugal separation at 14000 rpm for 15 min, and after repeating this operation, the supernatant was discarded, the precipitate was dried in a vacuum dryer, and it was dissolved in 30 µl of extra pure water. The solution was subjected to the agarose gel electrophoresis, thereby confirming that DNA was separated alone.

In order to remove RNA, it was allowed to undergo a reaction in 500 µl of an RNase solution (composition: 100 µl of the above-mentioned DNA isolated solution and 5 µl of RNase (5 g/ml) at 37° C. for 1 hr, and an equal amount of the PCI solution (composition: a solution obtained by centrifuge at 13000 rpm for 5 min and by separating an aqueous layer after mixing phenol/chloroform/isoamyl alcohol (25:24:1) gradually) was added to the reaction solution. After putting a lid and gradually mixing, it was centrifuged at 13000 rpm for 5 min.

The aqueous layer (upper layer) was transferred to a new micro tube, to which an equal amount of the CIA solution (composition: chloroform/isoamyl alcohol, ratio by volume 24:1) preserved at room temperature was added, and after gradually mixing, it was centrifuged at 15000 rpm for 3 min, the aqueous layer was transferred to a new micro tube, followed by the CIA treatment one more time, 3 M sodium acetate of a quantity of 1/10 time that of the supernatant obtained and 100% ethanol of 2.5 times in quantity were added thereto, followed by mixing well, and cooling at –20° C. for 20 min or longer, and then it was centrifuged at 15000 rpm for 15 min, thereby pelletizing DNA, the supernatant was discarded, and after adding to the pellets 1 ml of 70% ethanol which had been cooled down, it was centrifuged at 15000 rpm for 15 min, the supernatant was discarded, and after adding 1 ml of 70% ethanol which had been cooled down, it was centrifuged at 15000 rpm for 15 min, the supernatant was discarded, and it was dried for 5 min by use of a desiccator under a reduced pressure.

With the genome DNA thus obtained as a template, using PCR composition (Table 4), a 35 cycle reaction was carried out at 94° C. (30 seq), 55° C. (30 sec), and 72° C. (120 sec), and thereafter, it was allowed to undergo a reaction at 72° C. for 10 min. After the reaction, it was kept at 4° C. and a PCR amplified product was obtained. When the DNA band in the PCR amplified product was confirmed by the 1% agarose gel electrophoresis, a characteristic DNA fragment was confirmed at a position which is about 2000 bp lower as shown in the Morita of FIG. 1.

TABLE 4a

| PCR Reaction (20 µl) | |
|---|---|
| Template DNA (1 ng/µl) | 5 µl |
| Primer mix (16 pmol/µl each) | 0.5 µl each |
| AO6*(SEQ ID NO: 1: ACTGGCCGAGGG) | |
| A48*(SEQ ID NO: 2: CCGCAGGGACCA) | |
| dNTP (2.5 mM each) | 1.6 µl |
| 10× buffer | 2 µl |
| distilled water | 7.9 µl |
| rTaq (Takara) | 0.5 µl |
| $MgCl_2$ | 2 µl |

*AO6 and A48 primers are made by BEX Corp.

Similarly, DNA bands obtained by treating similarly to the above are shown in FIG. 1 for the SN variety (SN) and the SS variety (SS) having Stevioside as the main component and Rebaudioside A as a secondary component.

The Morita variety has the characteristic base sequence at a position which is about 2000 bp lower and thus it can be distinguished easily from other varieties by detecting DNA by the agarose electrophoresis.

By using primers which are different from the above, the Morita variety and the SN variety were compared.

The DNA extraction was carried out by the CTAB method. About 0.5 g each of leaves from the Morita variety and the SN variety were frozen with liquid nitrogen in a mortar, the leaves were crushed by a pestle. Each crushed sample was mixed with 20 ml of a 2% CTAB solution (100 mM tris-HCl (pH 8.0) 20 mM, EDTA (pH 8.0), 2% CTAB, 1.4 M NaCl, 1% PVP) in a 50 ml Falcon tube, followed by incubation at 65° C. for 30 min. An equal amount of chloroform/isoamyl alcohol (24:1) was added thereto, followed by stirring for 10 min, and then it was subjected to centrifugal separation at 3500 rpm for 15 min, and the aqueous layer was taken in another 50 ml Falcon tube.

Furthermore, an equal amount of 100% isopropanol was added thereto, followed by centrifugal separation at 3500 rpm for 15 min, the precipitate was collected by a hook, which was transferred to a 1.5 ml micro tube. After rinsing the precipitate with 75% ethanol, it was dried and then dissolved in 600 µl of TE buffer. After adding 1 µl of a RNase solution (1 mg/ml) and incubating at 37° C. for 1 hr, an equal amount of TE saturated phenol was added thereto, followed by mixing and centrifugal separation at 15000 rpm for 30 min. The aqueous layer was moved to another micro tube, followed by the addition of 3M sodium acetate of 1/10 in quantity and an equal amount of isopropanol, and mixing, and then it was subjected to centrifugal separation at 15000 rpm for 30 min. After rinsing the precipitate thus obtained with 75% ethanol twice, it was dried, which was dissolved in 50 µl of TE buffer to make a DNA sample.

With the DNA sample thus obtained as a template, the PCR reaction was allowed to take place with the following reaction composition. As to the PCR cycle, after allowing the reaction to occur at 96° C. for 30 sec, 35 cycles at 96° C. for 10 sec, at 42° C. for 2 min, and 72° C. for 2 min were allowed to take place, and then it was reacted again at 72° C. for 4 min. After the reaction, the PCR product was fractioned by the 1.8% agarose gel electrophoresis and after staining it with EtBr, the image was taken under UV irradiation. As a result, the specific band of the Morita variety could be confirmed in the neighborhood of about 2000 bp with the primer-UBC-66. In addition, specific bands of the SN variety were confirmed in the neighborhood of about 600 bp with the primer UBC-72, and in the neighborhood of about 700 bp with UBC-106. As a result, it has become clear that the Morita variety and the SN variety are genetically different and the difference can be easily detected by the RAPD analysis.

TABLE 4b

| PCR Reaction (50 µl) | |
| --- | --- |
| 10× PCR buffer | 5 µl |
| dNTP (2.0 mM) | 5 µl |
| RAPD primer* (10 mer) | 5 µl (5 µM) |
| UBC-66: (SEQ ID NO: 3 GAGGGCGTGA) | |
| UBC-72: (SEQ ID NO: 4 GAGCACGGGA) | |
| UBC-106: (SEQ ID NO: 5 CGTCTGCCCG) | |
| Blend Taq (trade name) (Toyobo) - | .5 µl (2.5 U/µl) |
| Stevia DNA | 1 µl (30 ng/µl) |
| Sterilized water | 33.5 µl |

Example 2

Production of a Sweetener

Twenty g of dried leaves of the Morita variety obtained at the end of September were extracted with water of 20 times in quantity several times until no sweetness could be tasted, the solution was allowed to flow through a column packed with 20 ml of a cation exchange resin (Amberlite IR-120B), and a column packed with 20 ml of an anion exchange resin (Duolite A-4) and 5 ml of granular activated carbon, the solution which had passed through the column was allowed to flow through a column packed with 100 ml of an adsorption resin (Diaion HP-20), thereby adsorbing the sweetening components, and after sufficiently washing with water, it was dissolved in 300 ml of ethanol. The eluent thus obtained was concentrated under a reduced pressure, and dried, thereby obtaining powder of light yellowish white color. For the sake of comparison, sweetening components were obtained from TD and SN by similar treatments, and analyzed.

| | |
| --- | --- |
| Analysis method | high performance liquid chromatography |
| Column used | I libar Licrosorb NH$_2$ 5µ 4 mm (dia) × 250 mm |
| Flow rate | 1.5 ml/min |
| Development solvent | acetonitrile:water = 82:18 |
| Measurement wavelength | 210 nm |

The results of analysis of the extracted and refined products are given in

TABLE 5

Comparison test 3 of the Morita variety, TD and S

| Variety | ST (%) | RA (%) | RA/ST | Yield |
| --- | --- | --- | --- | --- |
| Morita | 5.7 | 75.9 | 13.3 | 3.52 g |
| TD | 6.1 | 71.2 | 11.6 | 3.25 g |
| SN | 53.2 | 21.0 | 0.39 | 2.20 g |

Sensory test 1: Each 0.1% solution of the Morita and SN obtained in Example 2 and a 0.1% solution of the yellow powder were separately prepared, and 10 panel participants who were very familiar with the taste of *Stevia* sweeteners were selected. And bitterness, astringency and sweetness quality were compared.

TABLE 6

Sensory Test 1

| | No. stating Morita tastes bitter | No. stating SN tastes bitter |
| --- | --- | --- |
| Bitterness | 0 | 10 |
| | No. stating Morita tastes astringent | No. stating SN tastes astringent |
| Astringency | 0 | 10 |
| | No. stating Morita sweetenss is superior | No. stating SN sweetness is superior |
| Sweetness | 10 | 0 |

In each of the samples, the Morita variety has been improved in bitterness and astringency in comparison with other samples, and its sweetness is superior.

Sensory test 2: Each 0.1% solution of the Morita and TD obtained in Example 2 that are the light yellow powder were separately prepared, and 10 panel participants who were very familiar with the taste of *Stevia* sweeteners were selected. And bitterness, astringency and sweetness quality were compared.

TABLE 7

Sensory Test 2

| | No. staing Morita tastes bitter | No. stating TD tastes bitter |
| --- | --- | --- |
| Bitterness | 2 | 8 |
| | No. stating Morita tastes astringent | No. stating TD tastes astringent |
| Astringency | 3 | 7 |
| | No. stating Morita sweetness is superior | No. stating TD sweetness is superior |
| Sweetness | 9 | 1 |

In each of the samples, the Morita variety has been improved in bitterness and astringency in comparison with other samples, and its sweetness is superior.

Example 3

Production of Rebaudioside A

After heating and dissolving 2 g of the extracted and refined product (Morita variety) obtained in Example 2 in 95% methanol of a volume of 10 times, it was allowed to stand at 4° C. for 6 days while cooling it down. The crystal thus obtained was separated, and after washing it with cold methanol, it was dried under a reduced pressure, and 1.2 g of a white crystal was obtained. For the sake of comparison, from TD and SN, 0.9 g of a white crystal and 0.6 g of a white crystal were obtained by a similar treatment, respectively and they were analyzed.

| | |
|---|---|
| Analysis method | high performance liquid chromatography |
| Column used | Hibar Licrosorb $NH_2$ 5µ 4 mm (dia) × 250 mm |
| Flow rate | 1.5 ml/min |
| Development solvent | acetonitrile:water = 82:18 |
| Measurement wavelength | 210 nm |

The results of analysis of the extracted and refined products are given in Table 8.

TABLE 8

Comparison test 4 of the Morita variety, TD and S

| Variety | ST (%) | RA (%) | RA/ST | Yield |
|---|---|---|---|---|
| Morita | 2.3 | 92.1 | 40.0 | 1.2 g |
| TD | 3.7 | 87.9 | 23.7 | 0.9 g |
| SN | 94.2 | 2.0 | 0.02 | 0.6 g |

Sensory test 3: Each of 0.1% solution of the white powder of SN obtained in Example 3 was prepared, and 10 panel participants who were very familiar with the taste of *Stevia* sweeteners were selected. Bitterness, astringency and sweetness quality were compared.

TABLE 9

Sensory test 3

| | No. stating Morita tastes bitter | No. stating SN tastes bitter |
|---|---|---|
| Bitterness | 0 | 10 |
| | No. stating Morita tastes astringent | No. stating SN tastes astringent |
| Astringency | 0 | 10 |

TABLE 9-continued

Sensory test 3

| | No. stating Morita sweetness is superior | No. stating SN sweetness is superior |
|---|---|---|
| Sweetness | 10 | 0 |

In each of the samples, the Morita variety has been improved in bitterness and astringency in comparison with other samples, and its sweetness is superior. The recovery rate of a high purity product thereof was superior.

Sensory test 4: Each of 0.1% solution of the white powder of TD obtained in Example 3 was prepared, and 10 panel participants who were very familiar with the taste of *Stevia* sweeteners were selected. And bitterness, astringency and sweetness quality were compared.

TABLE 10

Sensory test 4

| | No. stating Morita tastes bitter | No. stating TD tastes bitter |
|---|---|---|
| Bitterness | 2 | 8 |
| | No. stating Morita tastes astringent | No. stating TD tastes astringent |
| Astringency | 2 | 8 |
| | No. stating Morita sweetness is superior | No. stating TD sweetness is superior |
| Sweetness | 10 | 0 |

In each of the samples, the Morita variety has been improved in bitterness and astringency in comparison with other samples, its sweetness is superior and recovery rate of a high purity product there was also superior.

Example 4

Purification of Rebaudioside A

After heating and dissolving 2 g of the extracted and refined product (Morita variety) obtained in Example 2 in 75% methanol of a volume of 5 times, it was allowed to stand at 4° C. for 7 days while cooling it down. The crystal thus obtained was separated, and after washing it with cold methanol, it was dried under a reduced pressure, and 0.9 g of a white crystal was obtained and analyzed.

TABLE 11

Purification of RA

| Variety | ST (%) | RA (%) | RA/ST | Yield |
|---|---|---|---|---|
| Morita | 0.1 | 97.2 | 972 | 0.9 g |

What we claim is:

1. A *Stevia rebaudiana* plant, wherein said plant is:
   i) variety Morita representative seeds having been deposited at the International Depository (Receipt No. FERM BP-10353),
   ii) capable of producing at least an 13.3:1 weight ratio of Rebaudioside A to Stevioside, and
   iii) contains a 2000 bp band when analyzed by Random Amplified Polymorphic DNA (RAPD) using the primer of SEQ ID NO: 3 (GAGGGCGTGA).

2. A *Stevia rebaudiana* plant produced by crossing the plant of claim 1 with another *Stevia rebaudiana* plant.

3. A plant or portion thereof that can be obtained from the seeds of International Depository (Receipt No. FERM BP-10353).

4. A method for the production of a sweetener, comprising extracting the plant of claim 1 or a portion thereof with a solvent comprising water, removing said solvent, and producing a sweetener.

5. A method for the production of a sweetener, comprising extracting the plant of claim 2 or 3 a portion thereof with a solvent comprising water, removing said solvent, and producing a sweetener.

6. A method of producing Rebaudioside A, comprising extracting a plant or portion thereof that is derived from the seeds of International Depository (Receipt No. FERM BP-10353) with a solvent for Rebaudioside A, removing said solvent and producing Rebaudioside-A.

7. The method of claim 6, wherein said Rebaudioside-A is at least 92% pure.

8. The method of claim 6, wherein said Rebaudioside-A is at least 97% pure.

9. The method of claim 6, wherein the Rebaudioside A is further recrystallized and has a purity of 92% or higher.

10. The method of claim 6, further comprising crystallizing Rebaudioside A from 95% methanol to produce at least 40 parts Rebaudioside A to one part of Stevioside and said Rebaudioside A having a purity of at least 92.1%.

11. The method of claim 10, further comprising recrystallizing Rebaudioside A from 75% methanol to produce at least at least 972 parts Rebaudioside A to one part of Stevioside and said Rebaudioside A having a purity of at least 97.2%.

* * * * *

SEQUENCE LISTING

```
<160> NUMBER OF SEQ ID NOS: 5

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: primer

<400> SEQUENCE: 1
actggccgag gg                                                         12

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: primer

<400> SEQUENCE: 2
ccgcagggac ca                                                         12

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: primer

<400> SEQUENCE: 3
gagggcgtga                                                            10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: primer

<400> SEQUENCE: 4
gagcacggga                                                            10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: primer

<400> SEQUENCE: 5
cgtctgcccg                                                            10
```